United States Patent [19]

Coy et al.

[11] Patent Number: 4,505,897

[45] Date of Patent: Mar. 19, 1985

[54] CYCLIC PENTAPEPTIDES DISPLAYING SOMATOSTATIN ANTAGONISM AND METHOD OF TREATMENT OF MAMMALS THEREWITH

[75] Inventors: David H. Coy, New Orleans; William A. Murphy, Slidell, both of La.

[73] Assignee: The Administrators of the Tulane Educational Fund, New Orleans, La.

[21] Appl. No.: 501,321

[22] Filed: Jun. 6, 1983

Related U.S. Application Data

[63] Continuation-in-part of Ser. No. 484,770, Apr. 18, 1983, abandoned.

[51] Int. Cl.³ .................... C07C 103/52; A61K 37/02
[52] U.S. Cl. .............................. 514/11; 260/112.5 R; 260/112.5 S
[58] Field of Search ................. 260/112.5 R, 112.5 S; 424/177

[56] References Cited

U.S. PATENT DOCUMENTS 4,235,886  11/1980  Freidinger et al. .......... 260/112.5 S

OTHER PUBLICATIONS

*Chemical Abstracts*, 80, 460, (1974), Abst. No. 83616f.
*Chemical Abstracts*, 97, 876, (1982), Abst. No. 182876y.
Bach et al., J. Am. Chem. Soc., 104, No. 2, 572–576, (1982).
Parsons, *Peptide Hormones*, University Park Press, Baltimore.
Nutt et al., *Int. J. Pept Protein Res.*, 21(1), 66–73, (1983).

*Primary Examiner*—Delbert R. Phillips
*Assistant Examiner*—F. Moezie
*Attorney, Agent, or Firm*—Estelle J. Tsevdos; Alphonse R. Noé

[57] ABSTRACT

Novel cyclic pentapeptide somatostatin antagonists and method for increasing the release of growth hormone, insulin, and glucagon in mammals are described.

10 Claims, No Drawings

CYCLIC PENTAPEPTIDES DISPLAYING SOMATOSTATIN ANTAGONISM AND METHOD OF TREATMENT OF MAMMALS THEREWITH

RELATED APPLICATIONS

This application is a continuation of parent application, U.S. Ser. No. 484,770, filed Apr. 18, 1983, now abandoned.

The invention herein described relates to novel cyclic pentapeptide somatostatin antagonists and method for increasing the release of growth hormone, insulin, and glucagon in mammals therewith.

Mammalian somatostatin, which has the following tetradecapeptide sequence:

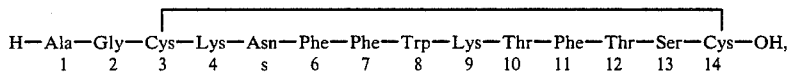

inhibits the release of growth hormone from the pituitary and insulin and glucagon from the pancreatic islet cells. It is also has inhibitory actions on numerous other endocrine and gastrointestinal activities in mammals. These inhibitory effects are well documented (c.f., P. Brazeau et al., Science 179: 77-79, (1973); W. A. Mortimer et al., Lancet 1: 697-701, (1974), and C. A. Meyers et al., in Gastrointestinal Hormones, edited by G. B. J. Glass, New York: Raven Press, 1980, pages 363-385, and their importance to the life cycle of mammals is clearly recognized.

Although hundreds of somatostatin analogs have been synthesized and evaluated in an attempt to find agonists, antagonists or competitive inhibitors of said hormone, no entirely satisfactory somatostatin antagonist or competitive inhibitor of this hormone has been available or disclosed in the art.

It is, therefore, an object of the present invention to provide a novel somatostatin antagonist effective for increasing release of growth hormone, insulin, and glucagon in mammals.

Surprisingly, this objective has been achieved with the synthesis of cyclo[Pro-Phe-D-Trp-Lys-Thr(Bzl)], and derivatives and pharmaceutically acceptable salts thereof.

The novel somatostatin antagonists of this invention are cyclic pentapeptides depicted by formula (I) and the pharmaceutically acceptable salts thereof, having the following amino acid sequence:

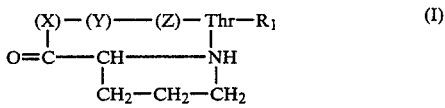

wherein X is phenylalanyl, tyrosyl, tryptophyl, 4-chlorophenylalanyl, 4-bromophenylalanyl, 4-fluorophenylalanyl, histidyl, 5-fluorotryptophyl, 5-chlorotryptophyl, 5-bromotryptophyl, 5-methoxytryptophyl, 5-methyltryptophyl, 4-methoxyphenylalanyl, 4-benzyloxyphenylalanyl, 4-methylphenylalanyl, or

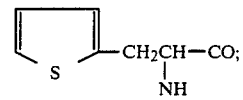

Y is D-tryptophyl, D-phenylalanyl, D-4-chlorophenylalanyl, D-4-bromophenylalanyl, D-4-fluorophenylalanyl, D-4-methoxyphenylalanyl, D-4-benzyloxyphenylalanyl, D-4-methylphenylalanyl, D-tyrosyl, D-5-fluorotryptophyl, D-5-bromotryptophyl, D-5-chlorotryptophyl, D-5-methoxytryptophyl, D-5-methyltryptophyl or D-histidyl; Z is lysyl or arginyl; Thr is threonyl and $R_1$ is hydrogen, benzyl or substituted benzyl, connected to the threonyl amino acid residue through its 3-oxygen atom.

The $R_1$ group referred to above may thus be illustrated as follows:

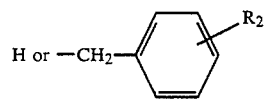

wherein $R_2$ is hydrogen, halogen (including fluorine, chlorine, bromine and iodine), $C_1$-$C_4$ alkoxy (preferably methoxy) or $C_1$-$C_4$ alkyl (preferably methyl).

Preferred compounds of the invention have the formula (I) structure wherein $R_1$ is hydrogen or benzyl; Z is lysyl, and X and Y represent chiral amino acid residues selected from those described for X and Y above.

An especially preferred cyclic pentapeptide somatostatin antagonist of this invention is the cyclo[Pro-Phe-D-Trp-Lys-Thr($R_1$)] which may be illustrated as follows:

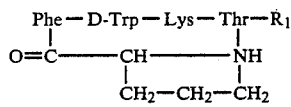

wherein Phe is phenylalanyl; D-Trp is D-tryptophyl; Lys is lysyl; Thr is threonyl, and $R_1$ is hydrogen or benzyl.

The term "pharmaceutically acceptable salts," as used in the present specification, is intended to mean non-toxic acid addition salts which are commonly used in the pharmaceutical industry. Among those of particular interest in the present invention are the hydrochloride, phosphate, sulfate, laurate, citrate, gluconate, succinate; acetate, and oleate salts of the formula (I) compounds. These salts are readily prepared by methods well known in the art.

In keeping with standard nomenclature, abbreviations for chiral amino acid residues used in the present specification and claims are as follows:

| Abbreviation | Name |
|---|---|
| Phe = | L-phenylalanyl |
| Tyr = | L-tyrosyl |

-continued

| Abbreviation | Name |
| --- | --- |
| Trp = | L-tryptophyl |
| (4-Cl)Phe = | L-4-chlorophenylalanyl |
| (4-Br)Phe = | L-4-bromophenylalanyl |
| (4-F)Phe = | L-4-fluorophenylalanyl |
| His = | L-histidyl |
| (4-CH$_3$)Phe = | L-4-methylphenylalanyl |
| (4-CH$_3$O)Phe = | L-4-methoxyphenylalanyl |
| (4-Bzl—O)Phe = | L-4-benzyloxyphenylalanyl |
| (5-F)Trp = | L-5-fluorotryptophyl |
| (5-Cl)Trp = | L-5-chlorotryptophyl |
| (5-Br)Trp = | L-5-bromotryptophyl |
| (5-CH$_3$O)Trp = | L-5-methoxytryptophyl |
| (5-CH$_3$)Trp = | L-5-methyltryptophyl |
| D-(4-F)Phe = | D-4-fluorophenylalanyl |
| D-(4-Cl)Phe = | D-4-chlorophenylalanyl |
| D-(4-Br)Phe = | D-4-bromophenylalanyl |
| D-(4-CH$_3$)Phe = | D-4-methylphenylalanyl |
| D-(4-CH$_3$O)Phe = | D-4-methoxyphenylalanyl |
| D-(4-Bzl—O)Phe = | D-4-benzyloxyphenylalanyl |
| D-Phe = | D-phenylalanyl |
| D-Tyr = | D-tyrosyl |
| D-Trp = | D-tryptophyl |
| D-(5-F)Trp = | D-5-fluorotryptophyl |
| D-(5-Br)Trp = | D-5-bromotryptophyl |
| D-(5-Cl)Trp = | D-5-chlorotryptophyl |
| D-(5-CH$_3$O)Trp = | D-5-methoxytryptophyl |
| D-(5-CH$_3$)Trp = | D-5-methyltryptophyl |
| D-His = | D-histidyl |
| Lys = | L-lysyl |
| Arg = | L-arginyl |
| Ala = | L-alanyl |
| Gly = | L-glycyl |
| Cys = | L-cysteinyl |
| Asn = | L-asparginyl |
| Ser = | L-seryl |
| Pro = | L-prolyl |

Other abbreviations used in the present specification are:
Bzl = benzyl
FMOC = fluorenylmethyloxycarbonyl
Boc = t-butyloxycarbonyl
HPLC = high performance liquid chromatography
TFA = trifluoroacetic acid
TLC = thin-layer chromatography In accordance with the process of the present invention, solid-phase synthesis of the formula (I) peptides can be carried out on a Beckman 990 automatic peptide synthesizer. Preparative HPLC can be performed on a thick-walled glass column (2.5×45 cm) containing Whatman LRP-1 reverse phase packing (C$_{18}$ silica 13–20 μm) pumped with Fluid Metering Company pump and pulse damper; and amino acid analyses can be run on a Beckman 119 CL analyzer and processed with a System AA computing integrator.

Amino acid derivatives utilized in the preparation of the compounds of the present invention are available from several chemical supply houses including: Bachem, Inc., Torrance, Calif.; and Chemical Dynamics, Inc., Plainfield, N.J.

Conveniently, the formula (I) peptides of this invention, cyclo[Pro-(X)-(Y)-(Z)-Thr-R$_1$], can be prepared beginning with the appropriate α-amino protected amino acid coupled to an appropriate resin, such as a polystyrene resin with one-two percent by weight of divinyl benzene as a cross-linking agent.

Protecting groups for the amino acids include: t-butyloxycarbonyl, isopropyloxycarbonyl, diisopropyloxycarbonyl, benzyloxycarbonyl, cyclopentyloxycarbonyl, and the like; but, t-butyloxycarbonyl or isopropyloxycarbonyl are generally preferred.

In the process, FMOC-(Z)-[Boc-Thr(Bzl)]-Pro-(X)-(Y)-O-CH$_2$-resin is prepared beginning with the appropriate Boc-(Y)-Merrifield resin, where Y is D-Trp, D-Phe, D-Tyr, D-(5-F)Trp, D-(5-Br)Trp, D-(5-Cl)Trp, D-(5-OCH$_3$)Trp, D-(5-CH$_3$)Trp, D-(4-F)Phe, D(4-Cl)Phe, D-4-Br)Phe, D-(4-CH$_3$)Phe, D-(4-CH$_3$O)Phe, D-(4-Bzl-O)Phe, or D-His. The resin is placed in the reaction vessel of the peptide synthesizer which has been programmed to carry out the following work-wash cycle: (a) methylene chloride, (b) 33% TFA in methylene chloride, (c) methylene chloride, (d) ethyl alcohol, (e) methylene chloride, (f) 10% triethylamine in methylene chloride, and (g) methylene chloride.

The washed resin with the Boc group removed is then stirred with t-Boc-(X), where X is Phe, Tyr, Trp, (4-Cl)Phe, (4-Br)Phe, (4-F)Phe, (4-CH$_3$)Phe, (4-CH$_3$O)Phe, (4-Bzl-O)Phe, (5-F)Trp, (5-Cl)Trp, (5-Br)Trp, (5-CH$_3$O)Trp, (5-CH$_3$)Trp, His or

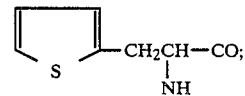

and diisopropylcarbodiimide in methylene chloride. The protected attached amino acids are then cycled through steps (b) through (g) in the above wash program. Thereafter, the following amino acids are coupled by the same cycle of events: t-Boc-Pro, t-Boc-Thr(R$_1$) and FMOC-(Z)-Boc, wherein R$_1$ is benzyl or substituted benzyl, and Z is Lys or Arg. These steps provide the FMOC-(Z)Boc-Thr-(R$_1$)-Pro-(X)-(Y)-O-CH$_2$-resin. Removal of the protected peptide from the resin by treatment with a ten-fold excess of hydrazine in methanol is accompanied by loss of the base-sensitive FMOC group to give H(Z)Boc-Thr(R$_1$)-Pro-(X)-(Y)NHNH$_2$, which is cyclized with hydrochloric acid and isoamylnitrite to give cyclo[Pro-(X)-(Y)-(Z)-Boc-Thr(R$_1$)]. Treatment of this peptide with 90% TFA in water containing 1% ethanedithiol then yields the desired somatostatin antagonist of this invention cyclo[Pro-(X)-(Y)-(Z)-Thr(R$_1$)]. These reactions are graphically illustrated in the Flow Diagram I below:

FLOW DIAGRAM I

FMOC—(Z)Boc—Thr(R$_1$)—Pro—(X)—(Y)—O—CH$_2$—resin

↓ NHNH$_2$/MeOH

H—(Z)Boc—Thr(R$_1$)—Pro—(X)—(Y)—NHNH$_2$

↓ HCl/i-amyl—NO$_2$

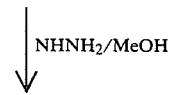

Cyclo[Pro—(X)—(Y)—(Z)Boc—Thr(R$_2$)]

↓ 90% TFA, 1% EDT

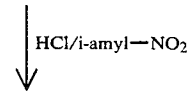

Cyclo[Pro—(X)—(Y)—(Z)—Thr(R$_1$)]

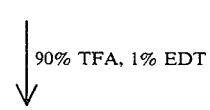

Alternatively, the compounds of this invention may also be prepared by the process hereinafter described.

After conventional solid-phase assembly beginning with 1 mmole of Boc-Phe-Merrifield resin (1% crosslinked), the protected peptide hydrazide, H-D-Trp-Lys(Cl-Z)-Thr(Bzl)-Pro-Phe-NHNH₂, is cleaved from the support by treatment with hydrazine in methanol and isolated by a procedure described by D. F. Veber et al., *Proceedings of the National Academy of Science, U.S.A.*, 75: 2636–2640, (1978). Without further purification, the hydrazide is converted to the azide, neutralized with triethylamine, and cyclized in DMF solution to yield the protected ninhydrin negative material, cyclo[-Pro-Phe-D-Trp-Lys-(Cl-Z)-Thr(Bzl)]. When this protected ninhydrin negative material is hydrogenated at atmospheric pressure and room temperature over 10% Pd on charcoal, the compound, cyclo[Pro-Phe-D-Trp-Lys-Thr(Bzl)], is formed and found to be a very effective somatostatin antagonist. When, however, the protected crude ninhydrin negative material is deprotected by treatment with HF-anisole under standard conditions, as described by G. T. Engberg et al., *Nature*, 293: 222–223, (1981), and purified by preparative HPLC eluting with 10–55% gradient of CH₃CN in 20% AcOH, the reaction yields the pure peptide, cyclo(Pro-Phe-D-Trp-Lys-Thr), which has somatostatin antagonist activity.

It is also found that HF treatment of the active somatostatin antagonist, cyclo[Pro-Phe-D-Trp-Lys-Thr(Bzl)], converts it to the peptide, cyclo(Pro-Phe-D-Trp-Lys-Thr), which also has somatostatin antagonist activity. The above reactions are graphically illustrated in Flow Diagram II below.

FLOW DIAGRAM II

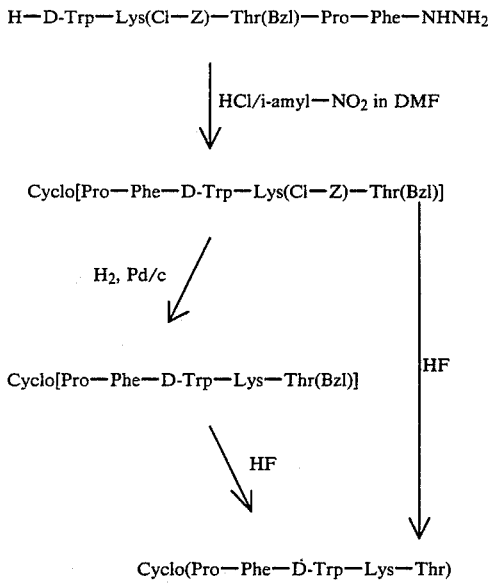

Among the cyclic pentapeptides of the present invention that display somatostatin antagonism and can be prepared by the process described and illustrated in Flow Diagram II above, are:
Cyclo[Pro-Phe-D-Tyr-Arg-Thr(Bzl)];
Cyclo[Pro-His-D-(5-F)Trp-Lys-Thr(Bzl)];
Cyclo[Pro-(4-F)Phe-D-Trp-Lys-Thr(3-F-Bzl)];
Cyclo[Pro-Phe-D-(5-CH₃)Trp-Lys-Thr(Bzl)];
Cyclo[Pro-Tyr-D-Tyr-Lys-Thr(Bzl)];
Cyclo[Pro-Phe-D-His-Lys-Thr(Bzl)];
Cyclo[Pro-Trp-D-Phe-Arg-Thr(Bzl)];
Cyclo[Pro-(4-Br)Phe-D-(5-Br)Phe-Lys-Thr(Bzl)];
Cyclo[Pro-Tyr-D-His-Lys-Thr(Bzl)];
Cyclo[Pro-Tyr-D-His-Arg-Thr(Bzl)];
Cyclo[Pro-Trp-D-Tyr-Lys-Thr(3-CH₃-Bzl)];
Cyclo[Pro-Phe-D-(4-F)Phe-Lys-Thr(Bzl)];
Cyclo[Pro-Phe-D-(4-Cl)Phe-Lys-Thr(Bzl)];
Cyclo[Pro-Phe-D-(4-Br)Phe-Lys-Thr(Bzl)];
Cyclo[Pro-Phe-D-(4-CH₃)Phe-Lys-Thr(Bzl)];
Cyclo[Pro-Phe-D-(4-CH₃O)Phe-Lys-Thr(Bzl)];
Cyclo[Pro-Phe-D-(4-Bzl-O)Phe-Lys-Thr(Bzl)];
Cyclo[Pro-(4-Me)Phe-D-Trp-Lys-Thr(Bzl)];
Cyclo[Pro-(4-CH₃O)Phe-D-Trp-Lys-Thr(Bzl)];
Cyclo[Pro-(4-Bzl-O)Phe-D-Trp-Lys-Thr(Bzl)];
Cyclo[Pro-Phe-D-Trp-Lys-Thr(Bzl)];
Cyclo[Pro-Phe-D-Trp-Arg-Thr(Bzl)];
Cyclo[Pro-Phe-D-Trp-Lys-Thr(4-Cl-Bzl)];
Cyclo[Pro-Phe-D-Trp-Lys-Thr(4-OCH₃-Bzl)];
Cyclo[Pro-Phe-D-Trp-Lys-Thr(4-CH₃-Bzl)];
Cyclo[Pro-Phe-D-Trp-Arg-Thr(3-Br-Bzl)];
Cyclo[Pro-Tyr-D-Trp-Lys-Thr(Bzl)];
Cyclo[Pro-Trp-D-Trp-Lys-Thr(Bzl)];
Cyclo[Pro-(4-Cl)Phe-D-Trp-Lys-Thr(Bzl)];
Cyclo[Pro-(4-F)Phe-D-Trp-Lys-Thr(Bzl)];
Cyclo[Pro-His-D-Tyr-Lys-Thr(Bzl)];
Cyclo[Pro-Trp-D-(5-OCH₃)Trp-Lys-Thr(Bzl)];
Cyclo[Pro-(4-Cl)Phe-D-Tyr-Arg-Thr(4-OCH₃-Bzl)];
Cyclo[Pro-Phe-D-Phe-Lys-Thr(Bzl)];
Cyclo[Pro-His-D-Phe-Lys-Thr(4-Cl-Bzl)];
Cyclo[Pro-Phe-D-(5-OCH₃)Trp-Lys-Thr(Bzl)], and
Cyclo[Pro-(4-Br)Phe-D-Tyr-Arg-Thr(Bzl)].
Cyclo(Pro-Phe-D-Tyr-Arg-Thr);
Cyclo[Pro-His-D-(5-F)Trp-Lys-Thr];
Cyclo[Pro-Phe-D-(5-CH₃)Trp-Lys-Thr];
Cyclo(Pro-Tyr-D-Tyr-Lys-Thr);
Cyclo(Pro-Phe-D-His-Lys-Thr);
Cyclo(Pro-Trp-D-Phe-Arg-Thr);
Cyclo[Pro-(4-Br)Phe-D-(5-Br)Phe-Lys-Thr];
Cyclo(Pro-Tyr-D-His-Lys-Thr);
Cyclo(Pro-Tyr-D-His-Arg-Thr);
Cyclo[Pro-Phe-D-(4-F)Phe-Lys-Thr];
Cyclo[Pro-Phe-D-(4-Cl)Phe-Lys-Thr];
Cyclo[Pro-Phe-D-(4-Br)Phe-Lys-Thr];
Cyclo[Pro-Phe-D-(4-CH₃)Phe-Lys-Thr];
Cyclo[Pro-Phe-D-(4-CH₃O)Phe-Lys-Thr];
Cyclo[Pro-Phe-D-(4-Bzl-O)Phe-Lys-Thr];
Cyclo[Pro-(4-Me)Phe-D-Trp-Lys-Thr];
Cyclo[Pro-(4-CH₃O)Phe-D-Trp-Lys-Thr];
Cyclo[Pro-(4-Bzl-O)Phe-D-Trp-Lys-Thr];
Cyclo(Pro-Phe-D-Trp-Lys-Thr);
Cyclo(Pro-Phe-D-Trp-Arg-Thr);
Cyclo(Pro-Tyr-D-Trp-Lys-Thr);
Cyclo(Pro-Trp-D-Trp-Lys-Thr);
Cyclo[Pro-(4-Cl)Phe-D-Trp-Lys-Thr];
Cyclo[Pro-(4-F)Phe-D-Trp-Lys-Thr];
Cyclo(Pro-His-D-Tyr-Lys-Thr);
Cyclo[Pro-Trp-D-(5-OCH₃)Trp-Lys-Thr];
Cyclo(Pro-Phe-D-Phe-Lys-Thr);
Cyclo[Pro-Phe-D-(5-OCH₃)Trp-Lys-Thr], and
Cyclo[Pro-(4-Br)Phe-D-Tyr-Arg-Thr].

The compounds of formula (I) are useful as somatostatin antagonists and are effective for increasing the release of growth hormone, insulin, and glucagon, in mammalian hosts, when administered thereto at dosages of from 0.000002 to 1 mg/kg of mammalian body weight per day.

The formula (I) compounds may be administered orally in the form of a feed additive or as a bolus, pill, tablet, oral gel, or the like, designed to deliver the active compound at the dosage level desired. They may also be administered parenterally by intramuscular, subcutaneous, intraperitoneal or intravenous injection, or as a transdermal or nasal spray.

As will hereinafter be shown, injection of formula (I) peptide into rats blocks the inhibitory effects of exogenous somatostatin on growth hormone, insulin, and glucagon release. In practice, it is also found that in fasted rats, basal hepatic portal insulin and glucagon levels are significantly increased after treatment with cyclo[Pro-Phe-D-Trp-Lys-Thr(Bzl)]; and, further, that plasma growth hormone levels in NEMBUTAL®*- anesthetized and stimulated rats are increased after injection with the above-said compound.

*NEMBUTAL ® sodium pentobarbital is a product of Abbott Laboratories.

The following examples further illustrate the present invention, but are not intended to be limitative thereof.

EXAMPLE 1

Preparation of
$N^{\alpha}$9-fluorenylmethyloxycarbonyl-$N^{\epsilon}$-tert-butyloxycarbonyl-L-lysyl-O-benzyl-L-threonyl-L-protyl-L-phenylalanyl-D-tryptophyl-O-CH$_2$ resin t-Butyloxycarbonyl-D-tryptophan-Merrifield resin (1% cross-linked, 2.5 g, 1.0 mmole) is placed in the reaction vessel of a Beckman Model 990 automatic peptide synthesizer programmed to carry out the following workwash cycle: (a) CH$_2$Cl$_2$; (b) 33% trifluoroacetic acid in CH$_2$Cl$_2$ (two times for one and 25 minutes each); (c) CH$_2$Cl$_2$; (d) C$_2$H$_5$OH; (e) CH$_2$Cl$_2$; (f) 10% (C$_2$H$_5$)$_3$N in CH$_2$Cl$_2$ (two times for two minutes each); (g) CH$_2$Cl$_2$.

The washed resin with the t-butyloxycarbonyl (Boc) group removed is stirred with t-butyloxycarbonyl-phenylalanine (t-Boc-Phe) and diisopropylcarbodiimide (3 mmole) in CH$_2$Cl$_2$ for one hour and the resulting amino acid resin then washed with CH$_2$Cl$_2$. The protected, attached amino acids are then cycled through steps (b) through (g) in the above wash program. The following amino acids (3 mmole) are then coupled successively by the same treatment cycle: t-butyloxycarbonyl-prolyl (t-Boc-Pro); t-butyloxycarbonyl-threonyl-benzyl [t-Boc-Thr(Bzl)] and fluorenylmethyloxycarbonyl-lysyl-t-butyloxycarbonyl [FMOC-Lys(Boc)].

Upon completion of the last coupling reaction, the resulting resin is washed with methanol to obtain the above-identified resinated product.

EXAMPLE 2

Preparation of
$N^{\epsilon}$-tert-butyloxycarbonyl-L-lysyl-O-benzyl-L-threonyl-L-prolyl-L-phenylalanyl-D-tryptophyl-NHNH$_2$ $N^{\alpha}$9-fluorenylmethyloxycarbonyl-$N^{\epsilon}$-tert-butyloxycarbonyl-L-lysyl-O-benzyl-L-threonyl-L-prolyl-L-phenylalanyl-D-tryptophyl-O-CH$_2$ resin (1.87 g, 0.5 mmol) is suspended in 70 ml of dry methanol and the thus prepared suspension then treated with 7 ml of anhydrous hydrazine. The mixture is stirred for 24 hours at ambient temperature and then filtered, washed with methanol and the methanol extracts evaporated to yield an oil that solidified upon trituration with ether to give 0.65 g of the above-named product in the form of a white powder.

EXAMPLE 3

Preparation of
cyclo(L-prolyl-L-phenylalanyl-D-tryptophyl-$N^{\epsilon}$-tert-butyloxycarbonyl-L-lysyl-O-benzyl-L-threonyl)

The peptide hydrazide $N^{\epsilon}$-tert-butyloxycarbonyl-L-lysyl-O-benzyl-L-threonyl-L-prolyl-L-phenylalanyl-D-tryptophyl-NHNH$_2$ (0.3 g, 0.33 mmol) is dissolved in 10 ml of dry dimethylformamide (DMF) and cooled to $-35°$ C. The solution is then acidified to pH 1.5 with hydrochloric acid in tetrahydrofurfuryl alcohol (HCl/THF) and isoamylnitrite (67 µl). The mixture is stirred at $-35°$ C. for 45 minutes and then added to 1.5 ml of dimethylformamide (DMF) and cooled to $-25°$ C. The reaction mixture is then neutralized to pH 7.5 with diisopropylethylamine and maintained at $-25°$ C. for 24 hours and 5° C. for an additional 24 hours. Evaporation of the DMF gives the above-identified product as a brown oil that exhibits a major spot by thin-layer chromatography (tlc).

EXAMPLE 4

Preparation of
cyclo(L-prolyl-L-phenylalanyl-D-tryptophyl-L-lysyl-O-benzyl-L-threonyl)

The fully protected peptide cyclo(L-prolyl-L-phenylalanyl-D-tryptophyl-$N^{\epsilon}$-tert-butyloxycarbonyl-L-lysyl-O-benzyl-L-threonyl) is dissolved in 50 ml of a mixture of trifluoroacetic acid, water, and 1,2-ethanedithiol prepared in a ratio of 45:5:2 by volume. The solution is stirred at ambient temperature for 40 minutes and then evaporated to an oil. The resulting oil is dissolved in 50% acetic acid and eluted on a column (2.5×95 cm) of Sephadex G-15 with 50% acetic acid. Lyophilized material from a major peak absorbing at 280 nm is then applied to a column of Whatman LRP-1 octadecylsilanesilica and eluted with a linear gradient of 10 to 15% acetonitrile in 20% acetic acid solution.

The major peak is collected and lyophilized to give the required peptide as a white, fluffy powder (90 mg). This material gives one Cl-starch, ninhydrin and Ehrlich reagent-positive spot with the following $R_f$'s on silica gel TLC plates: n-BuOH:AcOH:H$_2$O:EtOAc (1:1:1:1), 0.68; n-BuOH:AcOH:H$_2$O (4:1:1), 0.47; EtOAc:pyridine:AcOH:H$_2$O (5:5:1:3), 0.79; 2-PrOH:-1MAcOH (2:1), 0.61. Amino acid analysis of a sample hydrolyzed in methanesulfonic acid containing 0.1% tryptamine gives: Thr, 0.98; Pro, 1.01; Lys, 0.97; Trp, 0.85.

EXAMPLE 5

Preparation of
cyclo(L-prolyl-L-phenylalanyl-D-tryptophyl-L-lysyl-L-threonyl)

The dried peptide, cyclo(L-prolyl-L-phenylalanyl-D-tryptophyl-L-lysyl-O-benzyl-L-threonyl), is placed in a vessel suitable for HF cleavage. This vessel also contains a magnetic stirring bar. A small quantity of anisole sufficient to wet the peptide is added to this vessel. The vessel is next connected to an HF line and placed under vacuum to remove any air therein. The vessel is then cooled to about $-78°$ C. with a dry ice-acetone bath. Doubly distilled HF (about 10 ml/gm of peptide) is added to the vessel. The dry ice-acetone bath is then removed from the vessel and replaced by an ice-water bath. The vessel's contents are vigorously stirred for about 45 minutes while the vessel remains immersed in the ice-water bath. Most of the HF in the vessel is then removed by water aspiration. After the majority of HF is removed by water aspiration, the remaining HF and anisole are removed via a vacuum pump to afford the title peptide.

EXAMPLE 6

Evaluation of peptide effects on growth hormone, insulin, and glucagon release in mammals using the rat as the test species In this evaluation, the procedures described by W. A. Murphy et al., *Endocrinology*, 109:491–495 (1980), were employed.

In growth hormone (GH) experiments, male rats (Charles Rivers) were anesthetized with NEMBUTAL ® (5 mg per 100 g/BW) which also served to maintain stimulated plasma GH levels. Exactly 30 minutes after the rats were anesthetized, 0.5 ml of saline or the test peptide in saline was administered as a sc bolus. A 1 ml blood sample was drawn from the jugular vein 15 minutes after the injection. For examining blocking effects of the analog on somatostatin, the cyclic peptide was given five minutes prior to somatostatin. GH levels were determined using NIADDKD rat GH RIA components.

Data obtained are reported in Table I below.

TABLE I

Effects of the Cyclic Pentapeptides, the Compounds of the Present Invention, Cyclo[Pro—Phe—D-Trp—Lys—Thr(Bzl)] and the Unprotected Cyclo(Pro—Phe—D-Trp—Lys—Thr) Compared To Somatostatin on GH Levels in the Rat (Five Animals Per Group unless otherwise given).

|     | Peptide | Dose (μg/100 g body weight) | GH (ng/ml)* |
|-----|---------|---------|---------|
| (A) | Saline | — | 389 ± 60 (6) |
| (B) | Somatostatin | 0.4 | 152 ± 51 (5) |
| (C) | Cyclo(Pro—Phe—D-Trp—Lys—Thr) | 2 | 730 + 110 (6) |
| (D) | Cyclo(Pro—Phe—D-Trp—Lys—Thr | 10 | 459 ± 100 (5) |
|     | C + B | | 75 ± 29 (5) |
|     | D + B | | 114 ± 36 (4) |
| (A) | Saline | — | 648 ± 177 |
| (B) | Cyclo(Pro—Phe—D-Trp—Lys—Thr) | 0.3 | 1265 ± 318 |
| (C) | Cyclo(Pro—Phe—D-Trp—Lys—Thr) | 0.6 | 1072 ± 187 |
| (D) | Cyclo(Pro—Phe—D-Trp—Lys—Thr) | 1.2 | 728 ± 143 |
| (A) | Saline | — | 497 ± 80 |
| (B) | Somatostatin | 0.5 | 173 ± 46 (4) |
| (C) | Cyclo[Pro—Phe—D-Trp—Lys—Thr(Bzl)] | 0.2 | 1724 ± 393 |
| (D) | Cyclo[Pro—Phe—D-Trp—Lys—Thr(Bzl)] | 0.6 | 812 ± 163 |
|     | C + B | | 149 ± 73 |
|     | D + B | | 370 ± 73 |

* = Mean ± standard error (n).

From the above data, it can be seen that the compound of the present invention and an unprotected relative thereof were evaluated to determine the effects of both peptides on NEMBUTAL ®-stimulated GH release in rats. Radioimmunoassayable GH levels in control-stimulated jugular blood 648±177 ng/ml showed an increase to 1265±318 after injection with 0.3 μg/100 g body weight of the unprotected analog cyclo(Pro-Phe-D-Trp-Lys-Thr); whereas, the radioimmunoassayable GH levels in control-stimulated jugular blood of 497±80 ng/ml rose significantly to 1724±383 ng/ml after injection of 0.2 μg/100 g body weight of the compound of the invention, i.e., the protected compound cyclo[Pro-Phe-D-Trp-Lys-Thr(Bzl)].

From the above data, it appears that the antagonist effect of the compounds of the present invention is not wholly dependent on the presence of the aromatic benzyl protecting group on the threonine.

What is claimed is:

1. A cyclic pentapeptide compound having the structural formula:

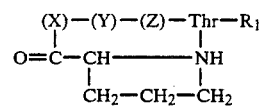

wherein

X is phenylalanyl;

Y is D-tryptophyl;

Z is lysyl; Thr is threonyl; and $R_1$ is hydrogen or benzyl; or a pharmaceutically acceptable salt thereof.

2. A compound according to claim 1, cyclo[Pro-Phe-D-Trp-Lys-Thr(Bzl)].

3. A compound according to claim 1, cyclo(Pro-Phe-D-Trp-Lys-Thr).

4. A method for increasing release of growth hormone, insulin and glucagon in mammals, said method comprising: administering thereto from 0.00001 to 1 mg/kg of mammalian body weight/day of a compound having the structural formula,

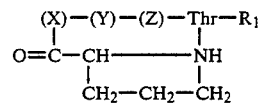

wherein

X is phenylalanyl;

Y is D-tryptophyl;

Z is lysyl; $R_1$ is hydrogen or benzyl;

or pharmaceutically acceptable salts thereof.

5. A method according to claim 4 for releasing growth hormone in mammals wherein the compound administered to said mammalian host is cyclo[Pro-Phe-D-Trp-Lys-Thr(Bzl)].

6. A method according to claim 4 for releasing growth hormone in mammals wherein the compound administered to said mammalian host is cyclo(Pro-Phe-D-Trp-Lys-Thr).

7. A method according to claim 4 for releasing insulin in mammals wherein the compound administered to said mammalian host is cyclo[Pro-Phe-D-Trp-Lys-Thr(Bzl)].

8. A method according to claim 4 for releasing insulin in mammals wherein the compound administered to said mammalian host is cyclo(Pro-Phe-D-Trp-Lys-Thr).

9. A method according to claim 4 for releasing glucagon in mammals wherein the compound administered to said mammalian host is cyclo[Pro-Phe-D-Trp-Lys-Thr(Bzl)].

10. A method according to claim 4 for releasing glucagon in mammals wherein the compound administered to said mammalian host is cyclo(Pro-Phe-D-Trp-Lys-Thr).

* * * * *